United States Patent
Skourlis

(10) Patent No.: US 9,488,627 B2
(45) Date of Patent: Nov. 8, 2016

(54) AUTOMATED STATIONARY GAS SENSOR CALIBRATION SYSTEM AND METHOD

(76) Inventor: James Skourlis, Pittsburgh, PA (US)

(\*) Notice: Subject to any disclaimer, the term of this patent is extended or adjusted under 35 U.S.C. 154(b) by 336 days.

(21) Appl. No.: 14/235,403

(22) PCT Filed: Jul. 29, 2011

(86) PCT No.: PCT/US2011/045883
§ 371 (c)(1),
(2), (4) Date: Jan. 27, 2014

(87) PCT Pub. No.: WO2013/019178
PCT Pub. Date: Feb. 7, 2013

(65) Prior Publication Data
US 2014/0349408 A1    Nov. 27, 2014

(51) Int. Cl.
*G01N 21/27*    (2006.01)
*G01N 27/12*    (2006.01)
*G01J 5/52*    (2006.01)
*G01J 5/50*    (2006.01)
*G01N 33/00*    (2006.01)

(52) U.S. Cl.
CPC ........... *G01N 33/0006* (2013.01); *G01J 5/522* (2013.01); *G01N 21/27* (2013.01); *G01N 21/274* (2013.01); *G01N 27/127* (2013.01)

(58) Field of Classification Search
CPC ... B01J 19/0046; B01J 19/00; G01N 27/403; G01N 27/26; G01N 27/00; G01N 33/5438; G01N 33/54373; G01N 33/54366; G01N 33/543; G01N 33/53; G01N 33/50; G01T 1/16; G01J 5/522; G01J 5/52; G01J 5/50
USPC ...................................... 436/149; 422/83, 50
See application file for complete search history.

(56) References Cited

U.S. PATENT DOCUMENTS

| 3,195,554 A | 7/1965 | Hanna |
| 3,449,566 A | 6/1969 | Kolb et al. |
| 4,555,930 A | 12/1985 | Leach et al. |
| 8,236,257 B2 * | 8/2012 | Murakami ........... A61B 5/1486 204/409 |
| 2003/0000281 A1 | 1/2003 | Ketler |
| 2005/0263408 A1 | 12/2005 | Hazama |

FOREIGN PATENT DOCUMENTS

WO    WO 2007/126463    * 11/2007    ........... A61B 5/1495

OTHER PUBLICATIONS

International Search Report and accompanying Written Opinion for 2013/019178A1, 2013.
International Preliminary Report on Patentability for PCT/US2011/045883, 2012.
General specifications: MC1, AC1, AC4, AC8 Calibration Units, dated Jun. 30, 2008, pp. 1-8,; retrieved from the internet: www.yokogawa.com/us/is/downloads/pdf/analytical/0XYPDF/GS/MC1_GS_04.pdf.

\* cited by examiner

*Primary Examiner* — Christine T Mui
(74) *Attorney, Agent, or Firm* — Renner, Otto, Boisselle and Sklar LLP

(57) ABSTRACT

A stationary gas monitoring and testing system includes one or more gas monitoring stations 20, each of which includes at least one gas sensor. The system also includes a supply of testing span gas, a supply of testing zero gas, a gas distribution network connecting each gas sensor to the span gas supply and the zero gas supply through substantially separate conduits, and a controller for enabling the delivery of gas from the supply into the network for delivery to the one or more sensors. A one-way poppet valve at each gas monitor allows the supply conduits to be pressurized in advance. Pre-pressurized separate supply conduits minimize or eliminate the delay in delivering gas to each sensor for testing and calibration.

20 Claims, 3 Drawing Sheets

AUTOMATED STATIONARY GAS SENSOR CALIBRATION SYSTEM AND METHOD

FIELD OF THE INVENTION

The present invention is related to a stationary gas sensor system, and more particularly to a calibration system and method for stationary gas sensor systems.

BACKGROUND

Sensors for detecting hazardous gases are well known for monitoring potentially hazardous environments, such as mines and industrial facilities that use or produce combustible and other hazardous gases. These sensors must be exposed to the gas on a regular basis to ensure that the sensor is properly tested. This also helps to prevent annoying and costly false alarms, and failure to alarm when the gas reaches a dangerous level.

These sensors are tested by passing a gas of known fixed composition, from a supply, such as a compressed gas bottle, at a predetermined flow rate. Often a worker must visit each sensor within the facility and perform the testing at the sensor. If a supply of gas is not permanently provided at each sensor, the worker also must transport the gas, which by definition is hazardous. Most sensors require testing with both a span gas and a zero gas. A span gas is a gas containing a given amount of an impurity, the gas for which the sensor is designed to detect. A zero gas is a purified gas that has an impurity concentration below the minimum detection limit of the sensor.

SUMMARY

More particularly, the present invention provides a stationary gas monitoring and testing system that includes (i) one or more gas monitors, each of which includes at least one gas sensor, (ii) a supply of span gas, (iii) a supply of zero gas, (iv) a gas distribution network connecting each gas sensor to the calibration supply and the clearance supply through substantially separate conduits, and (v) a controller enabling the delivery of gas from the supply into the network for delivery to the one or more sensors.

An exemplary distribution network includes a span supply conduit connected to the span gas supply and a zero supply conduit connected to the zero gas supply, a manifold connected to the span supply conduit and the zero supply conduit through one-way poppet valves, and a test conduit connected to the pressure regulator to deliver gas from the manifold to the gas monitor.

The present invention can also provide a system with a plurality of gas monitors connected in series along the distribution network. Additionally or alternatively, the invention can provide a plurality of gas monitoring and testing systems, a remotely located controller, and a communication link between the remote controller and the controller in each monitoring and testing system.

The present invention also provides a method of testing multiple sensors in a stationary gas monitoring system substantially simultaneously, comprising the following steps: (a) opening a solenoid valve to pressurize a zero gas conduit between a supply of zero gas and the gas monitor; and (b) closing the solenoid valve in the zero gas conduit; (c) opening a solenoid valve to pressurize a testing span gas conduit between a supply of span gas and a gas monitor; (d) closing the solenoid valve in the span gas conduit.

The closing step typically either follows the corresponding opening step after a predetermined time or after the gas monitor transmits a signal indicating that gas from the corresponding supply has been detected by a sensor.

The sequence of operating the solenoid valves for both the zero gas conduit and the span gas conduit can be worked upon in a multiplicity of combinations.

Thus, the present invention can provide a calibration gas to a plurality of remotely located sensors in such a way that the sensors can be calibrated from a remote location. This means that a common supply of calibration span gas can be used to calibrate multiple remote sensors, and the span gas can be safely stored and resupplied in a single, secure location. This is particularly important for hazardous gases. To provide a consistent flow rate to each of the plurality of sensors from a single, remotely-located, pressurized source, the present invention employs separate distribution lines for the span gas and a clearance or zero gas, respectively. One-way valves at each monitoring station allow each distribution line to be filled with gas in advance so that it can be quickly supplied to each sensor in the system.

The foregoing and other features of the invention are hereinafter fully described and particularly pointed out in the claims, the following description and annexed drawings setting forth in detail certain illustrative embodiments of the invention, these embodiments being indicative, however, of but a few of the various ways in which the principles of the invention may be employed.

DETAILED DESCRIPTION

Figure 1:
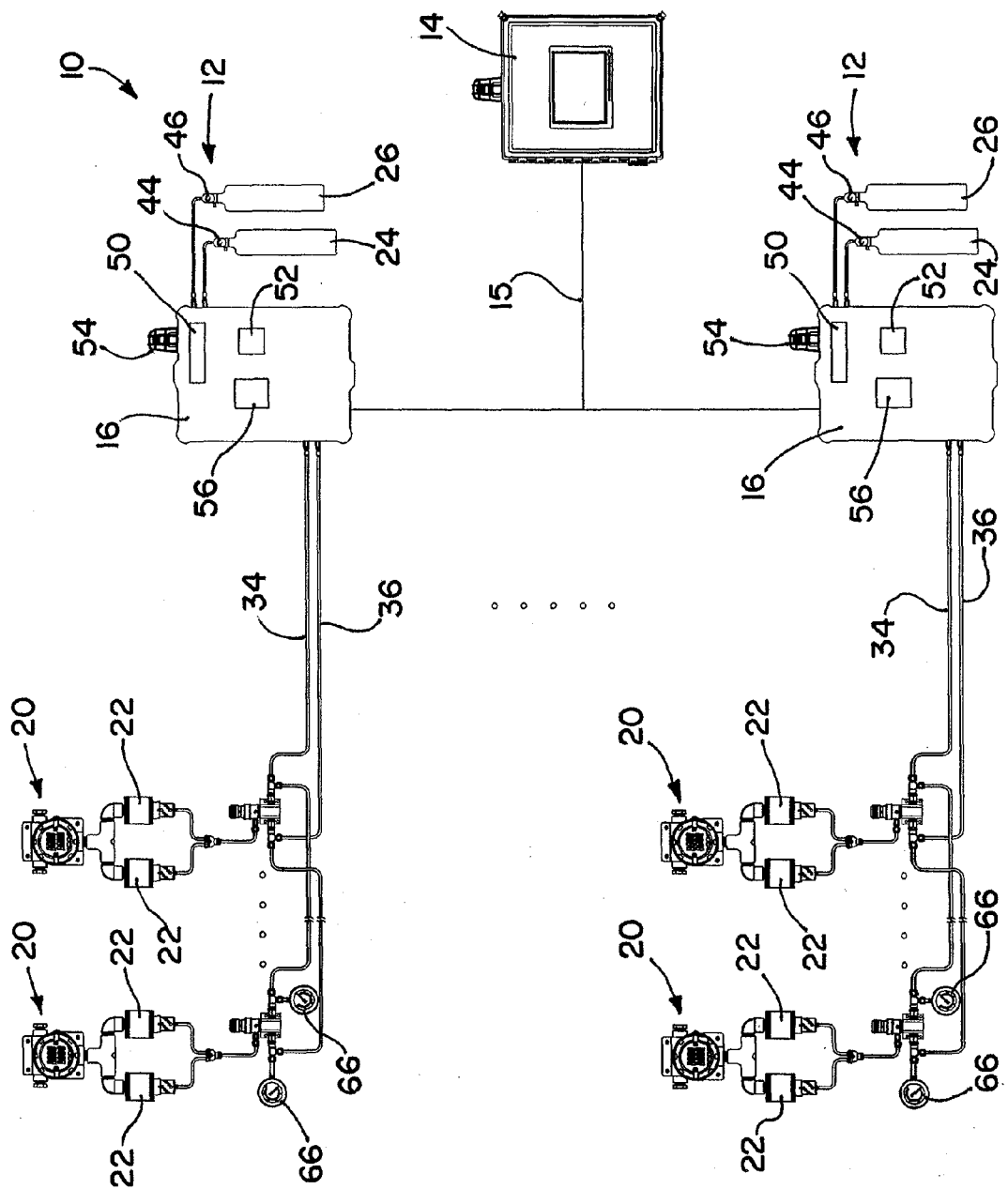
FIG. 1 is a schematic view of an exemplary global system provided in accordance with the present invention.

The present invention addresses the difficulty in supplying a testing gas to a plurality of remotely located sensors so that the sensors can be tested from a remote location. Thus a common supply of span gas can be used to test multiple remote sensors, and the testing gases can be safely stored and resupplied in a single, secure location. Applicant has recognized the difficulty, however, in providing a consistent flow rate to each of the plurality of sensors from a single, remotely-located, pressurized source. The present invention overcomes this difficulty by employing separate distribution lines for the span gas and a clearance or zero gas, respectively, and employs a regulator at each monitoring station to maintain a constant gas flow and a one-way poppet valve with a small cracking pressure that permits the gas lines to be pre-pressurized or primed.

Gas monitors that include one or more gas sensors (for example, electrochemical gas sensors, catalytic bead gas sensors, etc.) are used to monitor for one or multiple hazardous gases. Generally, gas from the environment to be monitored comes into contact with the sensors at the monitor. Electronics within the monitor convert the output signal from the sensors into one or more signals representative of a gas concentration. The sensor output per unit amount of gas can vary with age as well as environmental factors and hence periodic testing is required to ensure that the monitor reading is accurate.

Currently, gas monitoring sensors are calibrated by passing a testing gas having known, fixed compositions of one or more analyte gases from a compressed gas cylinder into contact with the sensor, displacing ambient air. The testing gas is allowed to flow until the sensor output reaches a steady state. Since the testing gas has a known composition, the output signal from each sensor can be adjusted to provide an accurate measure of analyte gas concentration. In the interval between full calibrations, an intermediate test (sometimes referred to as a bump test) can be performed to ensure that a sensor or instrument is responding to a specific analyte test gas in lieu of a full calibration sequence and as a method to verify sensor integrity and system response. A bump test generally involves exposing a sensor to a test gas for a brief period of time and to look for a minimum gas detection response from the gas monitor. As used herein, the terms "test" or "testing" refers generally to all types of analysis of the operation of a gas monitor and includes, for example, full calibration and bump testing.

Most sensors require testing with both a span gas and a zero gas. A span gas is a test gas containing a given amount of an impurity, the gas for which the sensor is designed to detect. A zero gas is a purified gas that has an impurity concentration below the minimum detection limit for most sensors, and also can be used to clear the span gas from the sensor at the end of the span gas test. For example, zero air (contains a mixture of 21% by volume oxygen with the balance of 79% by volume nitrogen) is an exemplary zero gas for a methane sensor, because it contains no methane. The system can provide a zero gas to a methane sensor at a steady flow rate, such as about 500 ml/min, and after a predetermined delay or when the sensor reaches a steady state, the zero control of the sensor can be adjusted to provide a zero gas detection reading. The system can then provide a span gas that contains a given amount of methane at or above the minimum detection limit of the methane sensor. After a predetermined time or when the sensor reaches a steady state, the sensor can be adjusted based on the gas detection reading that would be expected from the sensor for the given concentration of methane in the span gas.

Turning now to the drawings in detail, FIG. 1 shows an exemplary stationary gas monitoring and testing system. More particularly, FIG. 1 shows a global system 10 that includes one or more local monitoring and testing systems 12, and a remotely located controller 14 in connection with each of the local systems 12. Communication is provided by a communication link, such as a cable or wireless network 15 between the remote controller 14 and a respective test controller 16 in each local monitoring and calibration system 12.

Figure 2:
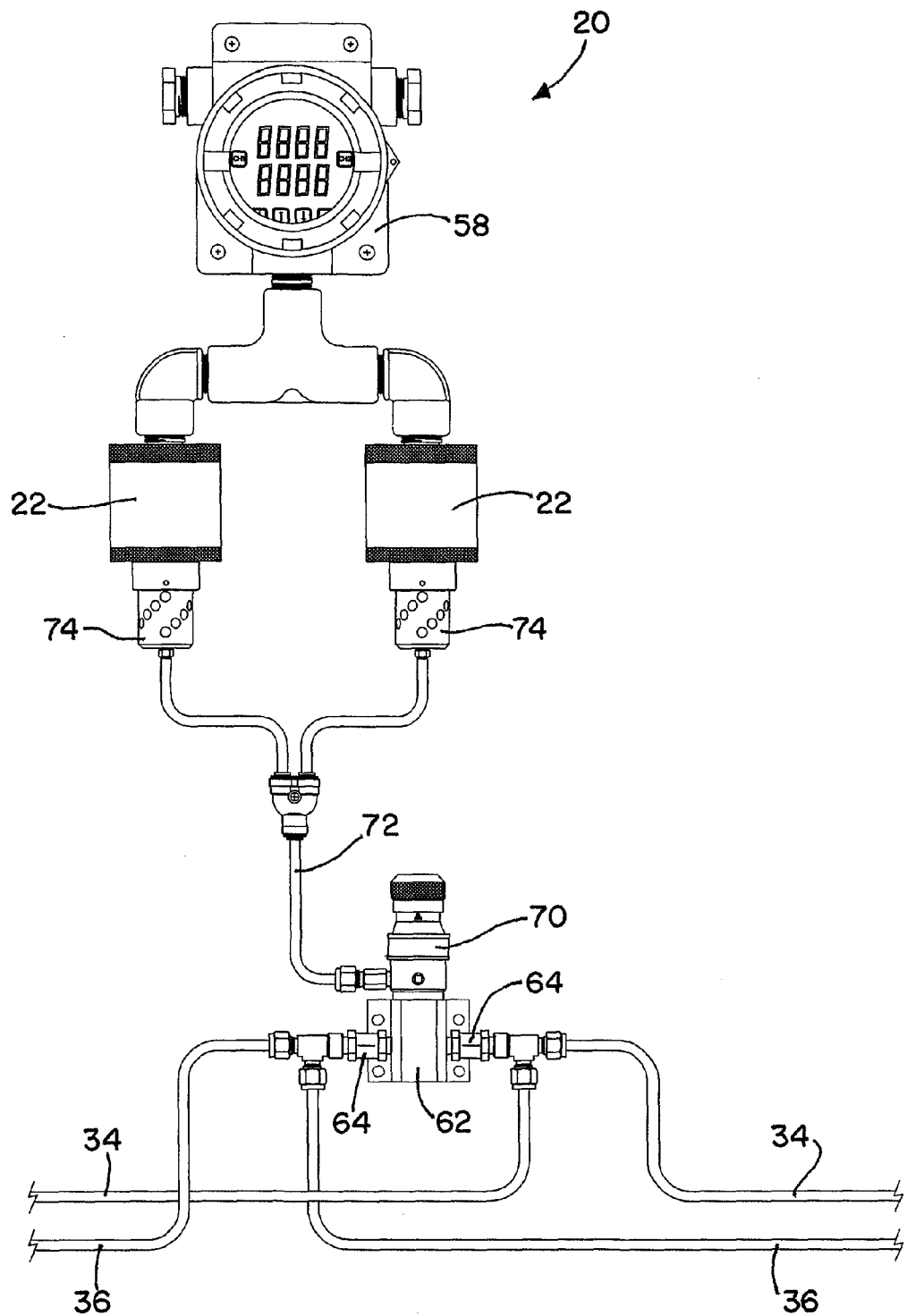
FIG. 2 is an enlarged view of an exemplary testing station of the system shown in FIG. 1.

Referring now to FIGS. 1 and 2, the local monitoring and testing system 12 includes (i) one or more gas monitoring stations 20, each of which includes at least one gas sensor 22, (ii) a supply of testing span gas 24 (also referred to as calibration gas), (iii) a supply of testing zero gas 26 (also referred to as clearance gas), (iv) a gas distribution network connecting each gas sensor 22 to the calibration supply 24 and the clearance supply 26 through substantially separate conduits 34 and 36, and (v) the previously-mentioned test controller 16 controlling the delivery of gas from the supply 24 and 26 into the network for delivery to the one or more sensors 22.

Each gas supply 24 and 26 is provided in a pressurized container that can be remotely stored and replaced as needed. An exemplary supply of calibration span gas includes a multiple-component gas that includes a combination of gases to be detected by the sensors. For example, the span gas can include one or more of carbon monoxide, hydrogen sulfide, oxygen, and a combustible gas, such as pentane. An exemplary span gas includes 100 parts per million of carbon monoxide, 19% by volume oxygen, 25 parts per million of hydrogen sulfide, 25% LEL (Lower Explosive Limit) pentane, with the balance being nitrogen. The supply of zero or clearance calibration gas 26 is selected to include no detectable amounts of the gases that most of the sensors might detect, and is used to clear the area adjacent to the sensor. An exemplary zero gas includes approximately 21% by volume oxygen and approximately 79% by volume nitrogen.

In the illustrated embodiment, each gas supply includes a pressure sensor 44 and 46 to indicate the pressure in the container. Additionally, each supply includes a regulator to control the pressure and flow of the test gas supplied from the container. The test controller 16 electrically controls a solenoid valve in the path between the supply of span gas 24 and each gas monitoring station 20 and a solenoid valve in the path between the supply of zero gas 36 and each gas monitoring station 20. These solenoid valves typically are adjacent to the gas supply containers and are located in non-hazardous or safe areas.

The test controller 16 typically includes or is connected to an output device 50, such as a printer, as well as an alarm speaker 52 or light 54 or both, and an input device, such as a keyboard or pointing device or touch screen display 56. The controller also can control an alarm device (not shown) nearby each monitoring station 20 that can be activated if a sensor 22 at that monitoring station 20 detects a dangerous condition. The system 12 further includes a communication link (not shown) between a local or remote display monitor 58 at each gas monitoring station 20 and the local test controller 16. The communication link can be provided by a wireless or hardwired communication line.

The gas distribution network includes a span supply conduit 34 connected to the span gas supply 24 and a zero supply conduit 36 connected to the zero gas supply 26. Polyurethane tubing is an exemplary conduit material. The distribution network is connected to a manifold 62 at each monitoring station 20 for distribution to the one or more sensors 22 at that monitoring station 20. The distribution network further includes at least one one-way valve 64, such as a poppet valve, at a distal end of each supply conduit 34 and 36 before reaching the manifold 62 at each gas monitoring station 20. This one-way valve 64 allows each supply conduit 34 and 36 to be pressurized with gas in advance, so that opening the valve 64, such as by increasing the pressure in the conduit 34 or 36, quickly dispenses gas from the supply conduit 34 or 36 to each sensor 22 at the monitoring station 20. Preferably, each valve 64 at each monitoring station 20 opens substantially simultaneously, thereby delivering calibration gas to each sensor 22 in the local system 12 substantially simultaneously. This allows many sensors 22 to be calibrated quickly. The distribution network further includes pressure gauges 66 at the distal ends of the each supply conduit 34 and 36 to monitor the pressure in the respective conduits 34 and 36.

At each monitoring station 20, a pressure regulator 70 is mounted to the manifold 62, and a test conduit 72 is connected to the regulator 70 to deliver gas to the sensors 22. The pressure regulator 70 preferably is adjustable to regulate the flow to the sensors 22 at the monitoring station 20. The test conduit 72 can include branches to direct the gas to multiple sensors 22. The test conduit 72 ends at an adapter 74, which couples the end of the test conduit 72 to a respective sensor 22.

Up to this point the gas distribution system is sealed from the environment. The adapter 74 (also referred to as a splash cup) provides a confined space adjacent to the sensor 22 for collecting testing gas and generally protects the sensor 22 from dirt and dust and other sources of damage in the environment. But the adapter 74 also provides a pathway, such as a plurality of holes or other openings, for gases in the ambient environment to reach the sensor 22. The pathway to the ambient environment also provides a pathway for the calibration gases to dissipate at the end of a calibration. Each monitoring station 20 also includes a local or remote display monitor 58 in communication with each sensor 22 at that station 20. Electronics sealed within the monitor 58 convert the output signal from the sensors 22 into one or more signals representative of a gas concentration, thereby enabling detection of hazardous concentrations. The monitor 58 can then issue an alarm to workers in the area, as well as signaling the local controller 16. It can also be seen by others skilled in the art that each monitoring station 20 can eliminate the local or remote display monitor 58 and communicate the output signal from sensors 22 into one or more signals representative of a gas concentration to a local controller 16.

Figure 3:
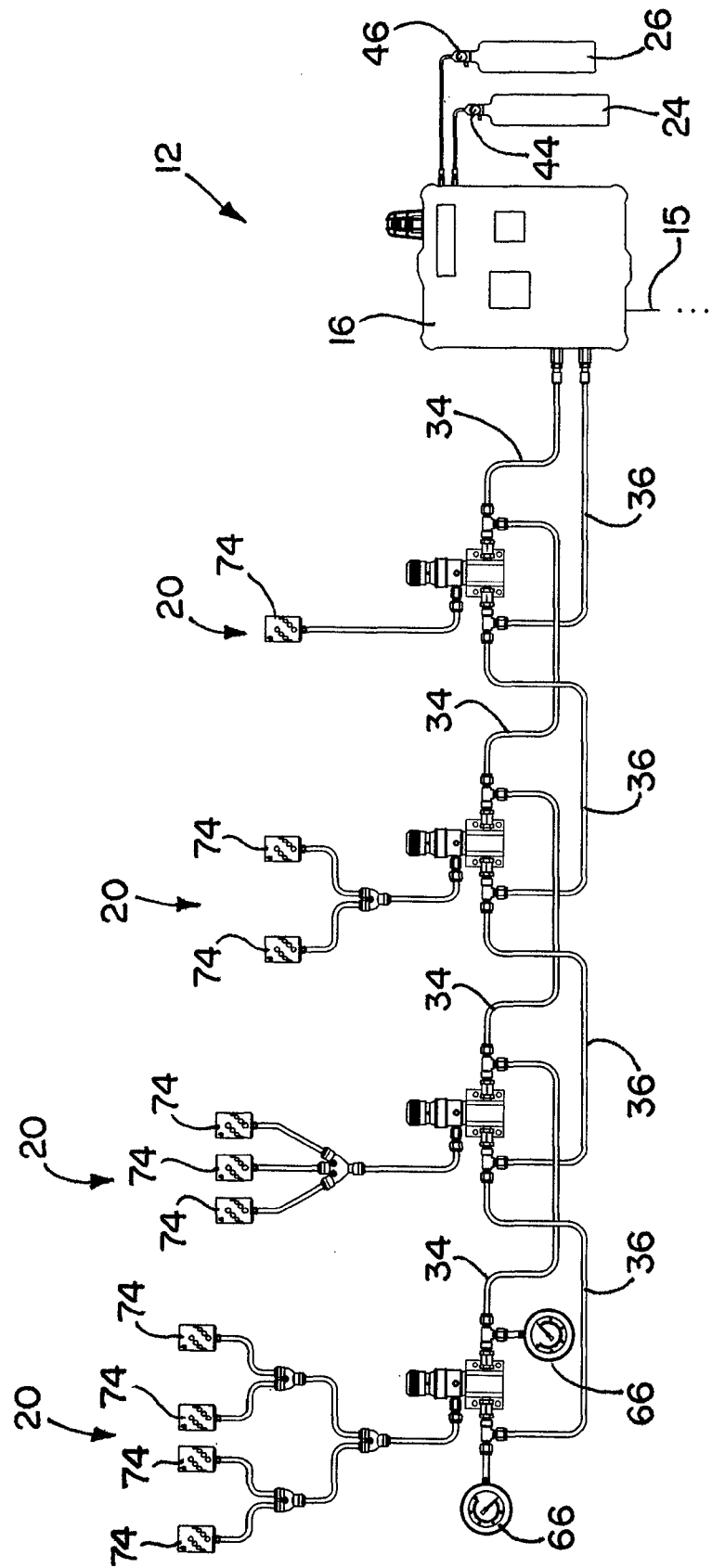
FIG. 3 is an enlarged view of an exemplary local system for use in the global system shown in FIG. 1, illustrating a variety of configurations for connecting the gas supply to each sensor.

The local system 12 can include a plurality of gas monitoring stations 20 connected in series along the distribution network. In the embodiment of FIG. 1, each of two gas monitoring stations 20 includes two gas sensors 22 connected in series. As shown in FIG. 3, however, the local system 12 can include a variety of gas sensors, including one, two, three, or four gas sensors per monitoring station 20, up to a total of about twelve sensors per local system. (Only adapters 74 are shown in FIG. 3.) At some point, additional sensors reduce the gas flow rate to one or more sensors to a rate that is too low for effective calibration. A preferred flow rate is about half a liter per minute per sensor. For more gas sensors, additional local systems 12 can be employed, and the test controller 16 for each local system 12 can be connected by a communication link 15 to the remote controller 14 (FIG. 1) as noted above.

A method of calibrating multiple sensors in such a stationary gas monitoring system substantially simultaneously includes the following steps: (a) opening a solenoid valve to pressurize a zero gas conduit between a supply of zero gas and the gas monitor; and (b) closing the solenoid valve in the zero gas conduit; (c) opening a solenoid valve to pressurize a calibration span gas conduit between a supply of span gas and a gas monitor; (d) closing the solenoid valve in the span gas conduit The method can further include the step of (e) transmitting a signal from the gas monitor to a remote controller.

The closing step (b) or (d) follows the corresponding opening step (a) or (c) either after a predetermined time or after the gas monitor transmits a signal indicating that gas from the corresponding supply has been detected.

In summary, the present invention provides a stationary gas monitoring and testing system 10 that includes one or more gas monitoring station 20, each of which includes at least one gas sensor 22. The system 10 also includes a supply of testing span gas 24, a supply of testing zero gas 26, a gas distribution network connecting each gas sensor 22 to the calibration supply 24 and the zero supply 26 through substantially separate conduits 34 and 36, respectively, and a controller 14 or 16 for controlling the delivery of gas from the supply into the network for delivery to the one or more sensors 22. A poppet one-way valve 64 at each gas monitoring station 20 allows the supply conduits 34 and 36 to be pressurized in advance. Pre-pressurized separate supply conduits 34 and 36 minimize or eliminate the delay in delivering gas to each sensor 22 for testing and calibration.

Although the invention has been shown and described with respect to a certain illustrated embodiment or embodiments, equivalent alterations and modifications will occur to others skilled in the art upon reading and understanding the specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function (i.e., that is functionally equivalent), even though not structurally equivalent to the disclosed structure which performs the function in the herein illustrated embodiment or embodiments of the invention.

I claim:

1. A stationary gas monitoring and testing system, comprising:
    a plurality of gas monitoring stations, each of which includes at least one gas sensor,
    a supply of testing span gas,
    a supply of testing zero gas,
    a gas distribution network connecting each gas monitoring station to the span gas supply and the clearance or zero gas supply through separate conduits, including a span supply conduit connected to the span gas supply and a zero supply conduit connected to the zero gas supply; and a one-way valve at a distal end of each supply conduit adjacent to each gas monitoring station to allow the supply conduits to be pre-pressurized; and
    a test controller enabling the delivery of gas from the supply into the network for delivery to the one or more sensors by controlling (i) a span gas valve in the path between the supply of span gas and each gas monitoring station, and (ii) a zero gas valve in the path between the supply of zero gas and each gas monitoring station.

2. A system as set forth in claim 1, where the supply of span gas includes a multiple-component gas that includes a combination of gases to be detected by the sensors.

3. A system as set forth in claim 1, where each gas monitoring station includes both a manifold connected to the span supply conduit and the zero supply conduit, and a test conduit connected to a pressure regulator to deliver gas from the manifold to the gas sensors.

4. A system as set forth in claim 1, where the one-way valve includes a poppet valve.

5. A system as set forth in claim 3, where the pressure regulator is interposed between the manifold and the test conduit to regulate the pressure and gas flow in the test conduit.

6. A system as set forth in claim 1, where the span gas valve includes a solenoid valve in the path between the supply of span gas and each gas monitoring station and the zero gas valve includes a solenoid valve in the path between the supply of zero gas and each gas monitoring station.

7. A system as set forth in claim 1, where the test controller includes or is connected to a display.

8. A system as set forth in claim 1, comprising a communication link between each gas monitoring station and the test controller.

9. A system as set forth in claim 1, where the supply of span gas is pressurized, and the supply of zero gas is pressurized.

10. A system as set forth in claim 1, where each supply includes a pressure sensor.

11. A system as set forth in claim 1, where the span gas includes one or more of carbon monoxide, hydrogen sulfide, oxygen and a combustible gas such as pentane.

12. A system as set forth in claim 1, where the zero gas includes approximately 21% oxygen and approximately 79% nitrogen.

13. A system as set forth in claim 1, where the span gas includes approximately 100 parts per million of carbon monoxide, 19% by volume oxygen, 25 parts per million of hydrogen sulfide, 25% LEL (Lower Explosive Limit) pentane, with the balance being nitrogen.

14. A system as set forth in claim 1, where each gas supply includes a regulator to control the pressure and flow of the gas supplied from the supply.

15. A system as set forth in claim 1, where the plurality of gas monitors are connected in series along the distribution network.

16. A plurality of the stationary gas monitoring and testing systems as set forth in claim 1, further comprising a remotely located remote controller, and, a communication link between the remote controller and the test controller in each of the stationary gas monitoring and testing systems of claim 1.

17. A method of testing multiple sensors in a stationary gas monitoring system substantially simultaneously, comprising the following steps:
 (a) opening a solenoid valve to pressurize a span gas conduit between a supply of span gas and a plurality of gas monitoring stations, each station having at least one gas sensor;
 (b) closing the solenoid valve in the span gas conduit;
 (c) opening a solenoid valve to pressurize a zero gas conduit between a supply of zero gas and the plurality of gas monitoring stations; and
 (d) closing the solenoid valve in the zero gas conduit.

18. A method as set forth in claim 17, comprising the step of transmitting a signal from the gas monitoring station to a remote controller.

19. A method as set forth in claim 17, where the closing step follows the corresponding opening step after a predetermined time.

20. A method as set forth in claim 17, where the closing step follows the corresponding opening step after the gas monitoring station transmits a signal indicating that gas from the corresponding supply has been detected.

* * * * *